(12) United States Patent
Johnson et al.

(10) Patent No.: US 7,638,119 B2
(45) Date of Patent: *Dec. 29, 2009

(54) METHOD OF DIMINISHING THE SYMPTOMS OF NEURODEGENERATIVE DISEASE

(75) Inventors: Jeffrey A. Johnson, Blanchardville, WI (US); Marcus J. Calkins, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/290,293

(22) Filed: Nov. 30, 2005

(65) Prior Publication Data

US 2006/0121014 A1 Jun. 8, 2006

Related U.S. Application Data

(60) Provisional application No. 60/632,373, filed on Dec. 2, 2004.

(51) Int. Cl.
*A61K 48/00* (2006.01)
*A61K 35/30* (2006.01)
*C12N 15/63* (2006.01)
*C12N 5/00* (2006.01)
*C12N 5/08* (2006.01)
*G01N 33/53* (2006.01)
*C12N 15/11* (2006.01)

(52) U.S. Cl. .................. 424/93.2; 424/570; 435/320.1; 435/325; 435/368; 435/7.1; 536/23.1

(58) Field of Classification Search ........................ None
See application file for complete search history.

(56) References Cited

OTHER PUBLICATIONS

Ridet et al., J Neurosc Res 72: 704-708, 2003.*
van Muiswinkel & Kuiperij, Curr. Drug Targets—CNS & Neurological Dis, 4: 267-281, 2005.*
Beal and Ferrante, Nat Rev 5: 373-384, 2004.*
Halliday et al Clin Exp Pharmacol Physiol 27: 1-8, 2000.*
Steece-Collier et al., PNAS USA 99(22): 13972-13974, 2002.*
Feigin et al., Curr Opin Neurol 15: 483-489, 2002.*
Gaura et al., Brain 127: 65-72, 2003.*
Lee et al., J Biol Chem 278: 12029-12038, 2003.*
Dakshinamoorthy and Jaiswal Oncogene 20: 3906-3917, 2001.*
Nguyen et al., Free Radical Biol and Med 37: 433-441, 2004.*
Calkins et al. Huntington's Disease Advocacy Center Article-1 page.*
Chicurel, M. HD Therapeutic pipeline, 2006.*
Bossy-Wetzel E, et al., "Molecular pathways to neurodegeneration," Nat. Med. 10: S2-9 (2004).
Calkins M, et al., "Protection from mitochondrial complex II inhibition in vitro and in vivo by Nrf2-mediated transcription," Proc. Natl. Acad. Sci. USA 102:244-249 (2005).
DiMauro S, et al., "Mitochondrial abnormalities in muscle and other aging cells: classification, causes, and effects," Muscle Nerve 26:597-607 (2002).
Emerit J, et al., "Neurodegenerative diseases and oxidative stress," Biomed. Pharmacother. 58:39-46 (2004).
Manfredi G & Beal F, "The role of mitochondria in the pathogenesis of neurodegenerative diseases," Brain Pathol. 10:462-472 (2000).
Schon E & Manfredi G, "Neuronal degeneration and mitochondrial dysfunction," J. Clin. Invest. 111:303-312 (2003).
Svendsen C & Langston J, "Stem cells for Parkinson disease and ALS: replacement or protection?," Nat. Med. 10:224-225 (2004).
Tabrizi S & Schapira A, "Mitochondrial abnormalities in neurodegenerative diseases," in Mitochondrial Disorders in Neurology vol. 2, 143-174 (Schapira A & DiMauro S. ed. 2002).

* cited by examiner

*Primary Examiner*—Jeffrey Stucker
*Assistant Examiner*—Aditi Dutt
(74) *Attorney, Agent, or Firm*—Quarles & Brady LLP

(57) ABSTRACT

A method of diminishing the symptoms of neurodegenerative disease in a patient is disclosed. In one embodiment, the method comprises the steps of: (a) identifying a patient with a neurodegenerative disease, (b) producing a cell culture, wherein the cell culture comprises cells with induced antioxidant response element (ARE) mediated transcription, and (c) transplanting at least a portion of the cell culture into the brain of the patient, wherein symptoms of neurodegenerative disease are diminished.

17 Claims, 7 Drawing Sheets

METHOD OF DIMINISHING THE SYMPTOMS OF NEURODEGENERATIVE DISEASE

CROSS-REFERENCE TO RELATED APPLICATION

This application claims the benefit of provisional application 60/632,373, filed Dec. 2, 2004, incorporated by reference herein.

STATEMENT REGARDING FEDERALLY SPONSORED RESEARCH OR DEVELOPMENT

This work was supported by NIEHS Grants ES 08089 and ES 10042. The United States Government has certain rights to this invention.

BACKGROUND OF THE INVENTION

The present invention is concerned with the treatment of neurodegenerative diseases, most particularly neurodegenerative diseases characterized by mitochondrial dysfunction.

The importance of mitochondrial dysfunction in neurodegenerative diseases, such as Huntington's Disease (HD), is underscored by the observation that complex II inhibitors produce a symptomology that is strikingly similar to HD, including select damage the medium spiny neurons of the striatum while sparing the aspiny neurons, and similar behavioral deficits (Ming, L., *J. Toxicol. Clin. Toxicol.* 33:363-367, 1995; Liu, X., et al., *Biomed. Environ. Sci.* 5:161-177, 1992; Ludolph, A. C., et al., *Can. J. Neurol. Sci.* 18:492-498, 1991; Palfi, S., et al., *J. Neurosci.* 16:3019-3025, 1996; Bossi, S. R., et al., *Neuroreport* 4:73-76, 1993). Consequently, the complex II inhibitors 3-nitropropionic acid (3NP) and malonate have been used extensively to model HD in vitro and in vivo (Brouillet, E., et al., *Prog. Neurobiol.* 59:427-468, 1999; Schapira, A. H., *Curr. Opin. Neurol.* 9:260-264, 1996). Like genetic models of HD, complex II inhibitors generate ROS (Perez-Severiano, F., et al., supra, 2004; Wyttenbach, A., et al., supra, 2002) as a direct consequence of disruption of the electron transport chain and excitotoxicity via a calcium influx through the N-Methyl D-Aspartate receptor (Reynolds, I. J. and T. G. Hastings, *J. Neurosci.* 15:3318-3327, 1995; Dugan, L. L., et al., *J. Neurosci.* 15:6377-6388, 1995; Albin, R. L. and J. T. Greenamyre, *Neuroloqy* 42:733-738, 1992). Additionally, the high concentration of striatal dopamine may contribute to ROS production and exacerbate the damage caused by complex II inhibition (Jakel, R. J. and W. F. Maragos, *Trends Neurosci.* 23:239-245, 2000). Striatal dopamine depletion attenuates damage caused by either 3NP or malonate in vivo (Maragos, W. F., et al., *Exp. Neurol.* 154:637-644, 1998). Conversely, enhanced dopamine release by methamphetamine potentiates 3NP (Reynolds, D. S., et al., *J. Neurosci.* 18:10116-10127, 1998).

One mechanism by which cells respond to oxidative insults is through the antioxidant response element (ARE), a cis-acting enhancer sequence that regulates the transcription of many cytoprotective genes. Upon toxic insult, glutathione depletion or chemical activation, the transcription factor Nrf2 translocates to the nucleus and dimerizes with small Maf proteins to form a trans-activation complex that binds to the ARE [For a review of Nrf2 regulation see Nguyen, et al., *Free Radic. Biol. Med.* 37:433-441, 2004]. Consequently, Nrf2-induced ARE activation coordinates the expression of many genes involved in combating oxidative stress and toxicity in a wide variety of tissues and cell types (Chan, K. and Y. W. Kan, *Proc. Natl. Acad. Sci. USA* 96:12731-12736, 1999; Ramos-Gomez, et al., *Proc. Natl. Acad. Sci. USA* 98:3410-3415, 2001; Cho, H. Y., et al., *Am. J. Respir. Cell Mol. Biol.* 26:175-182, 2002; Enomoto, A., et al., *Toxicol. Sci.* 59:169-177, 2001; Gao, X. and P. Talalay, *Proc. Natl. Acad. Sci. USA* 101:10446-10451, 2004; Lee, J. M., et al., *J. Biol. Chem.* 278:37948-37956, 2003; Thimmulappa, R. K., et al., *Cancer Res.* 62:5196-5203, 2002). In addition to protecting against chemical insults, carcinogenesis, and aging (Thimmulappa, R. K., et al., supra, 2002; Suh, J. H., et al., *Proc. Natl. Acad. Sci. USA* 101:3381-3386, 2004; Talalay, P. and J. W. Fahey, *J. Nutr.* 131:3027S-3033S, 2001; Zhang, Y. and G. B. Gordon, *Mol. Cancer Ther.* 3:885-893, 2004), Nrf2 has been shown to directly inhibit Fas-mediated apoptosis, a substrate for caspase-3-like proteases and an effector of PERK-mediated cell survival (Ohtsubo, T., et al., *Cell Death Differ.* 6:865-672, 1999; Kotlo, K. U., et al., *Oncogene* 22:797-806, 2003; Cullinan, S. B. and J. A. Diehl, *J. Biol. Chem.* 279:20108-20117, 2004; Cullinan, S. B., et al., *Mol. Cell Biol.* 23:7198-7209, 2003).

HD is an autosomal dominant neurodegenerative disorder that results from a polyglutamine repeat expansion in the in the first exon of the huntingtin gene (The Huntington's Disease Collaborative Research Group, *Cell* 72:971-983, 1993). Hallmarks of HD include severe degeneration of striatal medium spiny neurons and progressive choreiform movements (Graveland, G. A., et al., *Science* 227:770-773, 1985; Reiner, A., et al., *Proc. Nat. Acad. Sci. USA* 85:5733-5737, 1988). There are many proposed mechanisms of huntingtin-induced neuronal degeneration, yet no model fully explains the progression from mutation to cell death. Huntingtin aggregation, excitotoxicity, and oxidative stress have been suggested to play key roles in disease progression. However, the mechanism by which these factors arise and influence each other is largely unclear. Furthermore, it is unknown why striatal neurons are most susceptible to mutant huntingtin yet the protein is expressed ubiquitously.

One model of HD pathogenesis centers around mitochondrial dysfunction, excitotoxicity and subsequent reactive oxygen species (ROS) production (Calabrese, V., et al., *Neurochem. Res.* 26:739-764, 2001; Brown, S. E., et al., *Brain Pathol.* 9:147-163, 1999; Beal., M. F., *Ann. Neurol.* 38:357-366, 1995). Mitochondrial deficiencies, including reduced overall respiration and reduced activities of complex II, III and IV, have been measured in the striatum of post mortem HD brains (Gu, M., et al., *Ann. Neurol.* 39:385-389, 1996; Brennan, W. A., Jr., et al., *J. Neurochem.* 44:1948-1450, 1985). Similarly, reduced mitochondrial activity has been observed in at least one genetic mouse model of HD (Tabrizi, S. J., et al., *Ann. Neurol.* 47:80-86, 2000), and enhancement of electron transport by Coenzyme Q10 is effective in genetic models (Ferrante, R. J., et al., *J. Neurosci.* 22:1592-1599, 2002; Andreassen, O. A., et al., *Neurobiol. Dis.* 8:479-491, 2001; Ferrante, R. J., et al., *J. Neurosci.* 20:4389-4397, 2000; Schilling, G., et al., *Neurosci. Lett.* 315:149-153, 2001). HD patients also display increased ROS production in red blood cells and the striatum (Zanella, A., et al., *J. Neurol. Sci.* 47:93-103, 1980; Kuhl, D. E., et al., *Ann. Neurol.* 12:425-434, 1982; Martin, W. R., et al., *J. Neuroimaging* 5:227-232, 1995; Antonini, A., et al., *Brain* 119(Pt. 6):2085-2095, 1996) which is reflected in in vitro and genetic mouse models of HD (Andreassen, O. A., et al., supra, 2001; Hurlbert, M. S., et al., *Diabetes* 48:649-651, 1999; Perez-Severiano, F., et al., *Neurochem. Res.* 29:729-733, 2004; Wyttenbach, A., et al., *Hum. Mol. Genet.* 11:1137-1151, 2002).

Previously we have demonstrated that Nrf2-dependant transcription can prevent ROS-induced apoptosis in neurons and astrocytes in vitro (Lee, J. M., et al., supra, 2003; Lee, J. M., et al., *J. Biol. Chem.* 278:12029-12038, 2003; Shih, A. Y., et al., *J. Neurosci.* 23:3394-33406, 2003; Kraft, A. D., et al., *J. Neurosci.* 24:1101-1112, 2004; L1, J., et al., *Physiol. Genomics* 18:261-272, 2004).

In the Examples below, we demonstrate that Nrf2 and ARE-dependant signaling are critical mediators of the cellular response to mitochondrial inhibitors in vitro and in vivo. Furthermore, we show that further ARE induction can protect against complex II inhibitor toxicity.

BRIEF SUMMARY OF THE INVENTION

In one embodiment, the present invention is a method of diminishing the symptoms of neurodegenerative disease in a patient, comprising the steps of: (a) identifying a patient with a neurodegenerative disease, (b) producing a cell culture, wherein the cell culture comprises cells with induced antioxidant response element (ARE) mediated transcription, and (c) transplanting at least a portion of the cell culture into the brain of the patient, wherein symptoms of neurodegenerative disease are diminished.

In another embodiment, the present invention is the method described above wherein the cell culture is selected from the following cell types: astrocytes, human skin derived stem cells, hematopoietic stem cells and neural stem cells.

In another embodiment, the present invention is the method described above wherein the ARE mediated transcription is induced by infection of the cells with a vector comprising an ARE-inducing transgene, preferably Nrf2.

Preferably, the neurodegenerative disease is selected from the group consisting of Alzheimer's disease, Huntington's disease, Parkinson's disease, ALS disease, Friedreich's Ataxia, and AIDS dementia.

Additional embodiments and features of the present invention are apparent to one of skill in the art upon review of the specification, claims and drawings.

DETAILED DESCRIPTION OF THE INVENTION

In General

Figure 1:
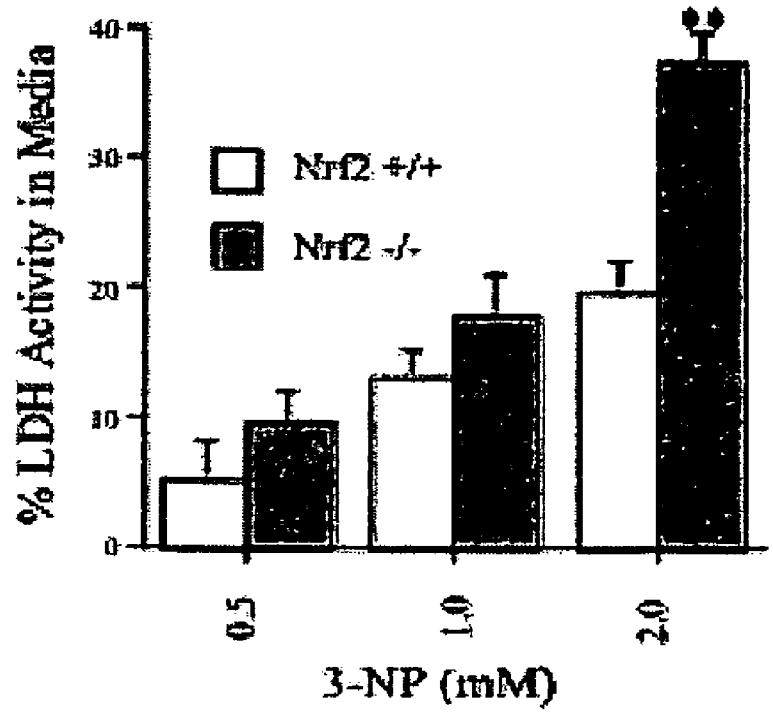
FIG. 1: Nrf2−/− primary neuronal cultures are more vulnerable to 3NP. Nrf2−/− and +/+ primary neuronal cultures were treated with 3NP. LDH release was measured (A), and TUNEL staining was performed (B). **$p<0.01$ as compared to WT.
Figure 1:
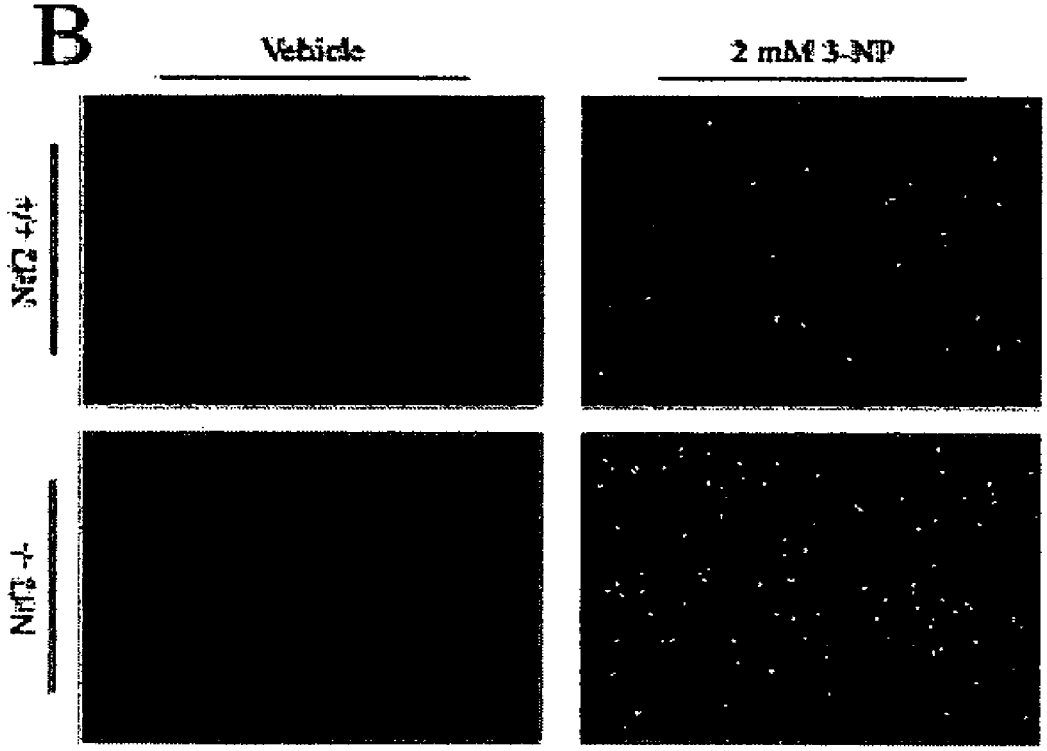

The Examples below describe induction of antioxidant response element mediated transcription in cells transplanted into mouse brain and show protection from a relevant neurodegenerative disease model. Most neurodegenerative diseases, such as Huntington's, Parkinson's, ALS and Alzheimer's, have a suspected or established oxidative stress component leading to pathology. Transcription mediated by the antioxidant response element is known to lead to cellular resistance to oxidative insult as well as other cytotoxic insults.

In order to stimulate transcription via the antioxidant response element in transplanted cells, primary astrocytes were infected with adenovirus overexpressing Nrf2 and injected into the striatum of mice; striatum is the brain region most affected in Huntington's Disease. Several weeks later, the mice were lesioned by intrastriatal injections of malonate, a mitochondria complex II inhibitor and commonly used chemical model for Huntington's Disease. Those mice receiving Nrf2 infected astrocyte transplants were dramatically more resistant to malonate lesions, when compared to mice receiving transplants of GPF control overexpressing astrocytes.

In one embodiment, the present invention is a method of diminishing the symptoms of neurodegenerative diseases in a patient. The method, in its most basic embodiment, comprises the steps of identifying a patient with neurodegenerative disease, producing a cell culture, wherein the cell culture comprises cells with induced antioxidant response element mediated transcription, and transplanting the cells into the brain of the patient.

Suitable Neurodegenerative Diseases

By "neurodegenerative disease" we mean any of a variety of diseases characterized by neuronal degeneration with a component of mitochondrial dysfunction and oxidative stress. (See Emerit, *Biomed. Pharmacol.*, 2004; Bossy-Wetzel, *Nature Med.*, 2004 for review). For example, the term "neurodegenerative disease" would include Alzheimer's disease, Huntington's disease, Parkinson's disease, ALS disease, Friedreich's Ataxia and AIDS dementia.

The following references review mitochondrial dysfunction in neurodegenerative disease and serve to illustrate our definition of "neurodegenerative disease": F. Beal, "Aging, energy, and oxidative stress in neurodegenerative diseases," *Ann. Neurol.* 38: 357-366 (1995); G. Manfredi and M. F. Beal, "The role of mitochondria in the pathogenesis of neurodegenerative diseases," *Brain Pathol.* 10: 462-472 (2000); E. A. Schon and G. Manfredi, "Neuronal degeneration and mitochondrial dysfunction," *J. Clin. Invest.* 111:303-312 (2003); S. DiMauro, K. Tanji, E. Bonilla, F. Pallotti and E. A. Schon, "Mitochondrial abnormalities in muscle and other aging cells: classification, causes, and effects," *Muscle Nerve* 26:597-607 (2002); and S. J. Tabrizi and A. H. V. Schapira, "Mitochondrial abnormalities in neurodegenerative diseases," In: A. H. V. Schapira and S. DiMauro, Editors, Mitochondrial Disorders in Neurology vol. 2, Butterworth-Heinemann, Boston, pp. 143-174 (2002).

Suitable Cell Culture

One would wish to use a suitable cell culture for induced ARE-mediated transcription.

Characteristics of a desirable cell for transplantation are:
(1) Survive transplant and have a substantial lifespan post transplant, preferably 2-3 months at a minimum,
(2) Long-term expression of introduced gene, preferably expressed for the entire lifetime of the cell or at least two-thirds of the lifetime,
(3) Capable of expressing factors specific to astrocyte ARE-driven response (see Shih, et al., *J. Neurosci.*, Apr. 15:28(8)3394-3406, 2003 and Kraft, et al., *J. Neurosci.*, Feb. 4:24(5)1101-1112, 2004 for rationale behind this concept),
(4) Transplantation of cells should not produce overtly negative effects in the patient (i.e. excessive immune response, graft rejection, tumor formation),
(5) Human cells (allografts) or non-human cells (xenografts) are both acceptable for the purposes of this invention (Fink, et al., *Cell Transplant*, Mar.-Apr.: 9(2) 273-278, 2000, Deacon, et al, *Nat. Med.* Mar. 3(3):350-353, 1997 are xenograft examples), and
(6) Other requirements found in Svendsen and Langston, *Nature Med.* 10(3):224-225, 2004. The Svendsen article addresses using neural progenitor cells as replacement technology (replacing dead neurons) versus protection (delivery systems for growth factors, etc.) and contains a list of proposed requirements for clinical trials, including a few points concerning neuronal protection trials and a few general points about all cellular therapy trials. These are specific points that would be at issue when proposing trials to the FDA and specifically relate to using neural progenitor cells as therapeutic devices.

Human-derived primary astrocytes may be the preferable cell type for transplantation. These are astrocytes that are cultured from human brain. Other specifically envisioned cell types are: hematopoietic stem cells which can be differentiated into neural stem cells and then astrocytes: (see Hao, et al., *J. Hematother. Stem Cell Res.* 12(1):23-32, 2003 and Jang, et al., *J. Neurosci. Res.* 75(4):573-584, 2004) and human neural progenitor cells, which can be differentiated toward astrocytes or non-differentiated. Other cell types that may be feasible include neural cells from stem cell sources (example; hematopoietic stem cells or human skin derived stem cells; both have been shown to be able to differentiate into astrocytes in rodent brain). Additionally, there is a technology in which cell lines (which may otherwise be tumorgenic) are encapsulated and implanted into brain (ventricles) where they then secrete certain factors necessary for cell protection (e.g., CNTF in Huntington's patients). We envision that this technology would be feasible with neuroblastoma cells or some other similar cell line. All cells used should mimic the Nrf2 response of astrocytes. Any cell type mentioned should be suitable across diseases.

Neural progenitor cells may be isolated, expanded and maintained according to Li, et al., *Toxicol. Sci.*, 83(2); 313=328, 2005 [Nov. 3, 2004, E-published ahead of print] and Svendsen, et al., *J. Neurosci. Meth.* 85(2):141-152, 1998. The referenced protocols are specific to maintaining neurosphere (neural progenitor cell) cultures.

In general, differentiation to astrocytes or different neuronal subtypes by a variety of neural progenitor cell types has been described (Bithell and Williams Clinical Science, 108 (1); 13-22, 2005 [2004; online manuscript CS20040276]). This review includes an example of astrocytes derived from a stem cell population (see refs. 63-66).

Human derived primary astrocytes which may be isolated and grown from patients prior to ex vivo gene therapy and reintroduction to donor have been described. See Ridet et al., "Isolation, Maintenance, and Adenoviral infection," *Hum. Gen. Ther.* 10:271-280, 1999; Serguera, et al., "Transplantation of Ad-infected human adult astrocytes into mammalian brain (mouse)," *Mol. Ther.* 3:875-881, 2001; Ridet, et al., "Transplantation of Retrovirally infected human adult astrocytes into mammalian brain," *J. Neurosci. Res.* 72:704-708, 2003; and Patent # WO 00/40699.

ARE Induction

The present invention requires the induction of ARE-mediated transcription in the selected cell type. This induction can be accomplished by several methods known to those of skill in the art, such as chemical induction. Specific examples of known chemical activators of the ARE include tert-butylhydroquinone, sulforaphane, curcumin, and diethylmaleate. In total nine classes of chemicals have been identified as ARE inducers. These include: "(i) oxidizable diphenols and quinines; (ii) Michael reaction acceptors (olefins or acetylenes conjugated to electron-withdrawing groups); (iii) isothiocyanates; (iv) hydroperoxides; (v) trivalent arsenic derivatives; (vi) divalent heavy metal cations ($Hg2+$, $Cd2+$); (vii) vicinal dithiols; (viii) 1,2-dithiole-3-thiones; and (ix) carotenoids and other conjugated polyenes" (quoted from Dinkova-Kostova, A. T., et al., *Proc. Natl. Acad. Sci. USA* Mar. 13, 98(6): 3404-3409, 2001).

In one embodiment, induction of the ARE-mediated transcription would be via infection with an ARE-inducing transgene, such as Nrf2. The examples below describe the Nrf2 gene and methods for isolating and obtaining this gene. Typically, one would present the gene on a viral vector. However, a viral vector is not absolutely necessary. It is a common way of introducing genes ex vivo. Another widely accepted way of introducing genes into mammalian cells is by transfection of DNA. Some (of many) methods of transfection include calcium phosphate mediated delivery, electroporation, gene gun and liposomal uptake methods.

The human Nrf2 gene can be obtained by cloning the sequence of *homo sapiens* nuclear factor (erythroid derived 2)-like 2 (NFE2L2) GenBank accession number NM_006164 from any human cell source. The clone can also be purchased from Origene, catalog number TC116283. Moi, et al. *Proc. Nat'l. Acad. Sci*, USA 91(21); 9926-30, 1994, reported the human gene.

The adenoviral vector we used in the Examples was created by the Canadian Stroke Network Adenovirus Core Facility (Vancouver, BC, Canada) (Kraft, et al., *J. Neurosci.* 24(5): 1101-1112, 2004). In the current form, it would be inappropriate for use in human patients. The Waisman Center at University of Wisconsin-Madison has successfully amplified the adenovirus vectors used for these studies. A biomanufacturing facility exists in the Waisman Center that has the capability to produce viruses (adenovirus, adeno-associated virus and/or lentivirus) suitable for use in human patients.

In the Example below, EGFP and the mouse Nrf2 gene from the pEF-Nrf2 vector (Alam, et al., *J. Biol. Chem.* 274: 26071-26078, 1999) were inserted into a replication deficient adenoviral construct created using the Cre-Lox system (Hardy, et al., *J. Virol.* 71:1842-1849, 1997). A separate CMV promoter drives expression of each gene. In order to overexpress Nrf2 in astrocytes, one would need to introduce into the cell a sequence of DNA containing the Nrf2 gene behind a functional promoter sequence. The promoter should contain all of the cis-factors necessary for recruitment of transcriptional proteins and successful initiation of transcription of the Nrf2 gene.

In an embodiment suitable for human use there should be no EGFP expression by the vector due to potential toxicity from overexpression of GFP. Transplanted cells should instead be labeled by an entirely innocuous means or not at all. The advantage to labeling cells is that post-mortem analysis of graft survival could then be accomplished easily. One example of how to achieve this aim without labeling would be to probe for cells that contain vector DNA using in situ hybridization techniques.

In order to prevent potential tumor formation as a result of transplants, it may be preferable to include a genetic component that will selectively kill proliferating transplanted cells. This concept is based on suicide gene therapy, which is currently being investigated for use with bone marrow transplants and potential cancer therapies. A kill switch would be important to stop excessive and unpredicted proliferation of cells. One approach, which has been examined in terms of cancer treatment, is to incorporate thymidine kinase expression into the cells. A prodrug like GANCICLOVIR can then be delivered systemically. Thymidine kinase will convert the prodrug to a toxic form, thus killing the proliferating cell. For example, see Vassaux, G. and P. Martin-Duque, *Export Opin. Biol. Ther.* Apr. 4(4):519-530, 2004 (Review); Goto, T., et al., *Mol. Ther.* Nov. 10(5):929-937, 2004; Berlinghoff, S., et al., *Lung Cancer* Nov. 46(2):179-186, 2004.

Non-adenoviral vectors would be appropriate and possibly preferable. For example, one may use lentiviral vector. The lentivirus is a commonly used retrovirus. It is conceivable that other retroviruses could be used as well. The advantage to using a retrovirus is that it will incorporate into the genome of the cells and will then be heritable. Adeno-associated virus is also an option that leads to incorporation into the genome of the cell. Thus cells overexpressing the transgene may be expanded prior to transplant. Adenovirus, adeno-associated virus, and lentivirus are the most common vectors for achieving ex vivo gene therapy; however, it is possible that other specific vectors may be used. Several types of adenovirus, adeno-associated virus, or lentivirus may be used depending on characteristics such as infectivity and stability of gene induction in the infected cell type.

Infection of Cells Prior to Transplant

Preferably, virus is added to cells 24 hours prior to transplantation. Typically, 50-200 pfu/cell (Multiplicity of Infection; MOI) would be added to the growing cells in basal media for 45 minutes in the 37° C. incubator, after which the conditioned media would be replaced and the cells would be allowed to recover overnight. The adenovirus we used in the examples is inappropriate for human use because it expresses EGFP and contains the mouse gene for Nrf2. EGFP may have some associated toxicity and the human gene would be preferable to the mouse for gene therapy. The adenovirus could easily be modified to remove the EGFP gene and should then be fine for use in ex vivo gene therapy in humans.

In order to modify the vector in the example for use with a lentivirus, we would simply swap out the adenoviral vector for the lentiviral vector. MOI at the time of infection would have to be optimized, such that we achieve >95% infection with little or not toxicity in culture.

Preparation of Cells for Transplantation (Adenovirus Infected Astrocytes)

The following is a prophetic description of how one would prepare infected cells for transplantation: One would first lift cells from dishes using trypsin. Cells would be lifted from plates using 0.25% trypsin for approximately 2 minutes or until the cells begin to detach from plates as viewed under the microscope. The cells would be washed 3× in basal media.

One would quantitate cells. Typically, live cells would be counted on a hemocytometer using the trypan blue exclusion method.

One would then suspend cells, preferably at $2 \times 10^7$ cells/ml, in basal media (MEM for example) immediately before injection.

Transplantation Procedure

The following is a prophetic transplantation procedure: One would first evaluate the number of cells to transplant. The number of cells transplanted should be approximately (±10%) $5 \times 10^6$ cells in 240 µl of basal media. This number is based on injections of 300,000 astroglial cells into the cebus apella brain (Lipina and Colombo, *Brain Res.* 911:176-180, 2001). Scaling up from the *cebus apella* monkeys, which were transplanted with 300,000 cells in 15 µl and using a total brain volume of 640 $cm^3$ for humans and 40 $cm^3$ for the monkey, we project a preferred dose of $5 \times 10^6$ cells in 240 µl liquid.

Targeted Brain Region

One would wish to target different brain regions for different neurodegenerative diseases. The probable target sites for transplantation are listed below for representative neurodegenerative diseases:

| | |
|---|---|
| Huntington's | Striatum (caudate and putamen) |
| Parkinson's | Substantia Niagra (mid-brain) |
| ALS | Brainstem, Spinal Cord |
| Alzheimer's | Frontal and Temporal Cortex, Hippocampus |

In Huntington's disease the transplant should be performed in both the caudate and the putamen as discussed in Huntington's transplantation references (Bachoud-Levi, et al., Lancet 356:1975-1979, 2000 and Hauser, et al., Neurology 58:687-695, 2002). A review of cell transplantation for Parkinson's disease can be found in Cellular and Molecular Neurobiology (Druker-Colin and Verdugo-Diaz, *Cell and Mol. Neuro.* 24(3):301-316, 2004); references for protocols should be found within. ALS transplantation possibilities and at least one trial are discussed in Silani, et al., *Lancet* 364(9429):200-202, 2004.

After-care (immune suppression, etc.) would preferably be according to previous transplantation trials.

Evaluation of Therapy

Patient evaluation would be according to previous transplantation trials. Preferably, evaluation of transplant success would be two-fold. First, one would assess survival of the transplants. Second, one would want to evaluate the progression of disease after transplantation.

In order to assess survival of the transplants in mice, we have relied on the expression of EGFP in the transplanted cells. Only about 5% of cells transplanted are visualized 5 weeks post-injection. This is likely due to two factors. First, not every cell is expected to survive transplantation. Second, there may be cells that are expressing only low levels of EGFP, which renders them invisible to the current method of detection. We have not been able to determine how each of these factors relates to the final surviving cell count. However, we have observed some cells' survival and have found that this number of cells is able to generate significant protection from mitochondrial toxins in mice.

Because we would want to remove the potentially toxic EGFP from any study in humans, we could not rely on a similar method for analyzing transplant survival. Instead we would need to create a new system of labeling. One possibility is to probe for the Nrf2 vector using in situ hybridization directed against DNA sequences specific to the vector. This would be a simple way to identify the Nrf2 overexpressing cells in a post-mortem analysis. In terms of evaluating symptoms, in general one would seek a decrease in the rate of disease progression, or possibly even an improvement of symptoms. Each disease has a standardized system of monitoring and quantifying symptoms and disease progression. Preferably, one would use these established measures as indicators of progression and/or improvement.

EXAMPLES

Example I

Protection from Mitochondrial Complex II Inhibition In Vitro and In Vivo by NRF2-Mediated Transcription Note: Example I is taken from Calkins, et al. *Proc. Natl. Acad. Sci. USA* 102:244-9, 2005, incorporated by reference herein.

Abstract

Huntington's disease is caused by a CAG repeat expansion in the huntingtin gene resulting in massive striatal degeneration. There is evidence that this cell loss is in part due to mitochondrial dysfunction. Complex II inhibitors 3-nitropropionic acid (3NP) and malonate cause striatal damage reminiscent of HD and have been used extensively as HD models. Previous research has shown that complex II inhibition involves oxidative stress. Because Nrf2-dependant transcriptional activation via the antioxidant response element is known to coordinate the upregulation of cytoprotective genes, we investigated the significance of Nrf2 in complex II-induced toxicity. We found that Nrf2-deficient cells and knockout mice are significantly more vulnerable to malonate and 3NP and demonstrate increased ARE-regulated transcription mediated by astrocytes. Furthermore, ARE-preactivation via intrastriatal transplantation of Nrf2-overexpressing astrocytes prior to lesioning conferred dramatic protection against complex II inhibition. These observations implicate Nrf2 as an essential inducible factor in the protection against complex II inhibitor-mediated neurotoxicity. These data also introduce Nrf2-mediated ARE transcription as a potential target of preventative therapy in HD.

Materials and Methods

Animals

Nrf2−/− and ARE-hPAP transgenic reporter mice were bred separately. Nrf2−/− mice were created by targeted disruption of the Nrf2 gene (Chan, K., et al., *Proc. Natl. Acad. Sci. USA* 93:13943-13948, 1996). ARE-hPAP reporter mice were created by insertion of a 51 basepair segment of rat NAD(P)H Quinone Oxidoreductase-1 promoter containing the core ARE into a minimal promoter upstream of the heat stable human Placental Alkaline Phosphatase (hPAP) (Johnson, D. A., et al., *J. Neurochem.* 81:1233-1241, 2002).

Chemicals and Antibodies

3NP and malonate were purchased from Sigma. Rabbit polyclonal anti-GFAP was purchased from DAKO, and monoclonal anti-β-III tubulin was purchased from Promega. Secondary antibodies, vector red alkaline phosphatase substrate, and nuclear fast red were purchased from Vector Labs. Fluorojade-B was purchased from Chemicon.

Primary Neuronal Culture

For primary cortical neuronal cultures, Nrf2+/− mice were bred and cultures were prepared from individual E15/16 embryos as previously described (Lee, J. M., et al., supra, 2003). Treatments were applied between day 3 and 5 in vitro. Immunostaining for β-III-tubulin and GFAP confirmed no difference in the ratio of neurons to astrocytes between genotypes (data not shown). HPAP+ cultures were prepared similarly. HPAP activity and histochemistry in primary cultures was measured as previously described (Johnson, D. A., et al., supra, 2002).

Cytotoxicity Measurements

LDH release into medium was measured using the CytoTox96 Non-Radioactive Cytotoxicity Assay kit (Promega) according to the manufacturers instructions. LDH activity was measured on both media and lysed cells. After normalizing to non-treated wells, the percentage of LDH in the media was calculated. Each measurement was made in at least triplicate on separate cultures from three individual pups. Terminal deoxynucleotidyltransferase-mediated dUTP nick end labeling (TUNEL; Roche Applied Science) staining was also performed according to the manufacturers instructions on cultures from at least two different pups per genotype.

3-NP Administration

Nrf2−/−, +/−, or +/+ mice received i.p. injections of 50 mg/kg 3NP or vehicle every 12 hours for a total of 7 injections. 25 mg/ml 3-NP in PBS was prepared fresh and adjusted to pH 7.4 with 10M NaOH. Individual doses were diluted so that injection volume remained constant at 200 μl. Six to eight hours after the last dose mice were sacrificed as below. One Nrf2 KO mouse died prior to the seventh dose and three others had severe symptoms that were classified as stage III according to Gabrielson, et al. (Gabrielson, K. L., et al., *Am. J. Pathol.* 159:1507-1520, 2001).

Behavioral Assessment for 3NP Treated Animals

To assess sensorimotor deficits in 3NP-treated animals, mice were trained up to 5 times per day on the rotarod (Columbus Instruments) for three days prior to 3-NP administration (Fernagut, P. O., et al., *Neuroscience* 114:1005-1017, 2002). All mice were able to achieve 180 sec (5 rpm) on the first trial by day three. Rotarod function was measured prior to the first dose and following the last dose of 3-NP.

Malonate Injections 18 week-old Nrf2 −/−, +/− and +/+ mice received malonate lesions by intrastriatal stereotaxic injection with contralateral vehicle injections. Mice were anesthetized with isoflurane. 0.5M malonate (1 µl; pH 7.4 in 0.9% NaCl) was injected 0.5 mm anterior to bregma, 2.1 mm lateral to midline, and 3.8 mm ventral to dura. One minute after insertion of the Hamilton syringe, the solution was administered over 2 minutes and the needle was withdrawn 2 mm per minute. ARE-hPAP+ mice were injected similarly with 0.25M (1 µl), due to differences in background strain sensitivity.

Histological Analysis

Mice were euthanized with $CO_2$ and perfused with 4% paraformaldehyde. Tissues were post-fixed overnight at 4° C. and cryoprotected in 30% sucrose/PBS. Using a cryostat (Leica), adjacent coronal 20 µm and 50 µm sections were taken for staining with Fluorojade-B and cresyl violet respectively through the entire striatum. Degenerating neurons were detected with Fluorjade-B according to the manufacturers suggested protocol. Lesion size was quantified using the Cavielieri Estimator (Stereoinvestigator; Microbrightfield) on sections 200 µm apart. HPAP histochemistry was measured as previously described (Johnson, D. A., et al., supra, 2002).

Primary Astrocyte Cultures and Transplantation

Primary astrocyte cultures were prepared from postnatal day 1/2 ARE-hPAP or wild-type pups as previously described (Lee, J. M., et al., supra, 2003). Nearly all cells (>95%) stained for the astrocyte marker GFAP after 7 days in culture (data not shown). After 5-7 days in culture, astrocytes were infected at 50 or 200MOI with recombinant adenoviral-Nrf2-GFP or adenoviral-GFP by a previously described protocol (Kraft, A. D., et al., supra, 2004). At 200MOI infection, greater than 95% of all cells expressed GFP after 24 hours. At 50MOI, about 70% expressed GFP after 24 hours.

Twenty-four hours post-infection, 100,000 (1 µl) cells were injected intrastriatally (using the same coordinates as above) into 13-18 week-old ARE-hPAP reporter or wild-type mice. Two mice received Ad-Nrf2-GFP infected astrocytes and two received Ad-GFP infected astrocytes bilaterally. Two other mice were injected with GFP-infected cells in one hemisphere and Nrf2-infected cells in the other. Mice were allowed to recover for 5 weeks and then lesioned with 0.5M malonate as described. One mouse from each group (bilateral Nrf2, bilateral GFP and GFP-left/Nrf2-right) received a malonate injection just lateral to the transplantation site (AP+0.5 mm, ML±2.4 mm, DV-3.8 mm). Mice receiving bilateral Ad-GFP or Ad-Nrf2 infected astrocyte transplants were lesioned in the right hemisphere.

Results

Nrf2−/− Primary Cultures are More Sensitive to 3NP than Nrf2+/+ Cultures

In order to examine the differential sensitivity of Nrf2−/− neurons to complex II inhibition, Nrf2+/+ and −/− primary cortical neuronal cultures (3 DIV) were treated with 3NP for 48 and assessed for LDH release. Vehicle-treated cultures showed no difference in LDH release, cellular morphology or culture composition between genotypes or compared to non-treated controls. At all doses, LDH release was greater in the Nrf2−/− cultures than in wild-type cultures. This trend was statistically significant at 2 mM 3NP (FIG. 1A). Nearly all Nrf2−/− neurons were TUNEL-positive as a result of treatment with 2 mM 3NP while a significantly lower percentage of Nrf2+/+ neurons were TUNEL-positive, as determined by visual inspection (FIG. 1B). In both Nrf2−/− and Nrf2+/+ cultures, TUNEL-positive cells were exclusively neuronal as confirmed by co-labeling with the neuronal marker NeuN (data not shown). This is in agreement with previous reports that neurons are selectively vulnerable to 3NP toxicity (Olsen, C., et al., Brain Res. 850:144-149, 1999).

hPAP Activation after 3NP Administration in Primary Neuronal Culture

Figure 2:
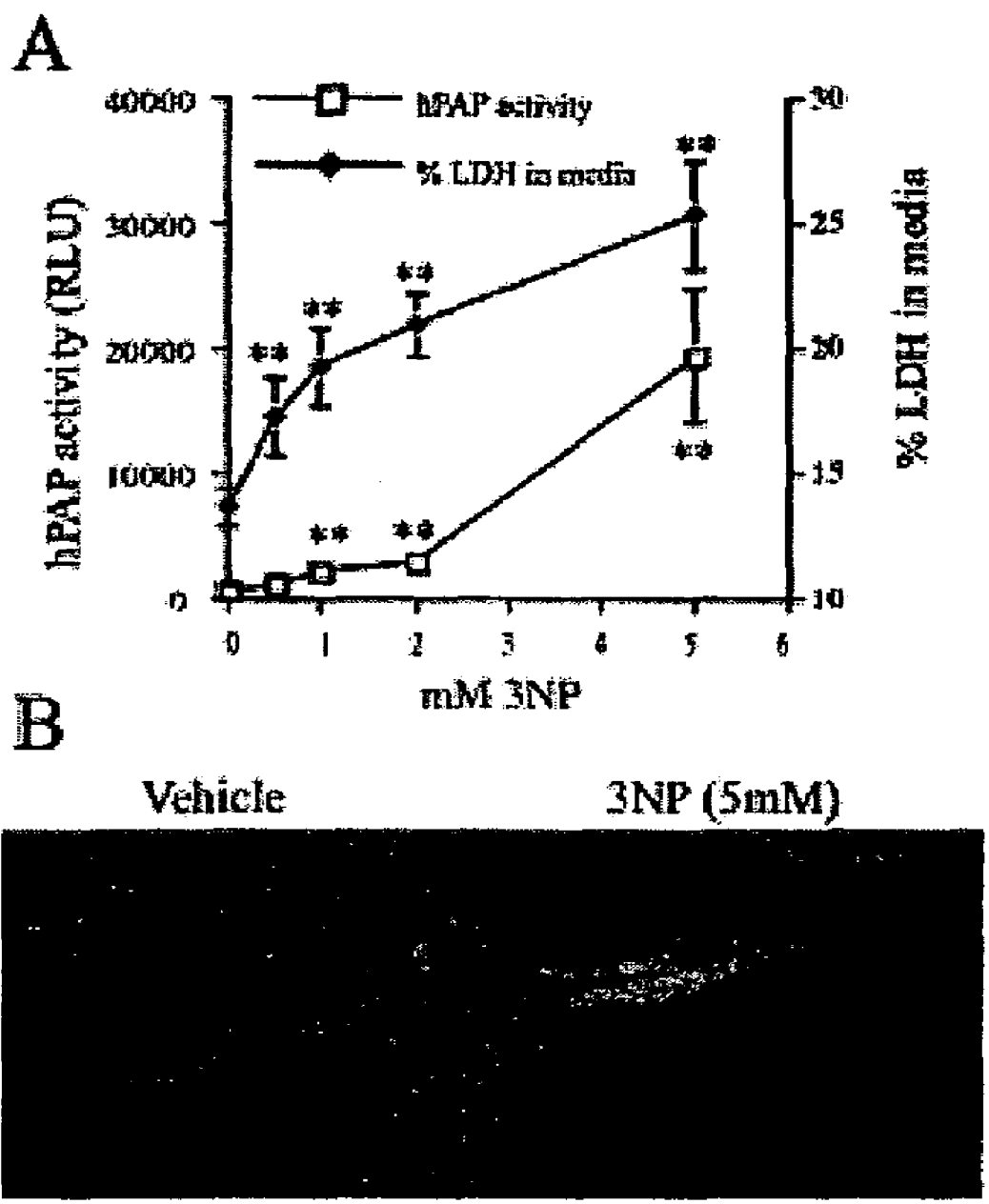
FIG. 2: hPAP expression resultant from 3NP treatment in primary neurons. ARE-hPAP primary neuronal cultures were treated with 3NP. LDH release and hPAP activation were measured (A). HPAP activity was visualized by vector red and GFAP was labeled with fluorescein (B).

To examine whether the ARE is activated in response to complex II inhibition, ARE-hPAP+primary cortical neuronal cultures were exposed to neurotoxic doses of 3NP. hPAP expression in neuronal cultures was significantly increased at 48 hours (FIG. 2A). This activation was localized to the surviving astrocytes (FIG. 2B) as visualized by vector red staining and GFAP co-labeling.

In Vivo Sensitivity of Nrf2−/−, Nrf2+/−, and Nrf2+/+ Mice to 3NP

We posited that this increased sensitivity would also extend to an in vivo model. 18 week-old mice were dosed every 12 hours with 50 mg/kg 3NP. After seven doses, a clear differential sensitivity had emerged based on the subjective classification described by Gabrielson, et al. (Gabrielson, K. L., et al., supra, 2001). Seven of eight Nrf2−/− mice rated at least stage 1, three were ranked stage III (endstage) and one mouse died prior to receiving the seventh dose (Table 1). In the Nrf2+/− group, only two out of six mice rated stage 1, and one out of six mice from the Nrf2+/+ group exhibited a stage I phenotype. No Nrf2+/+ or Nrf2+/− mice rated above stage 1.

Figure 3:
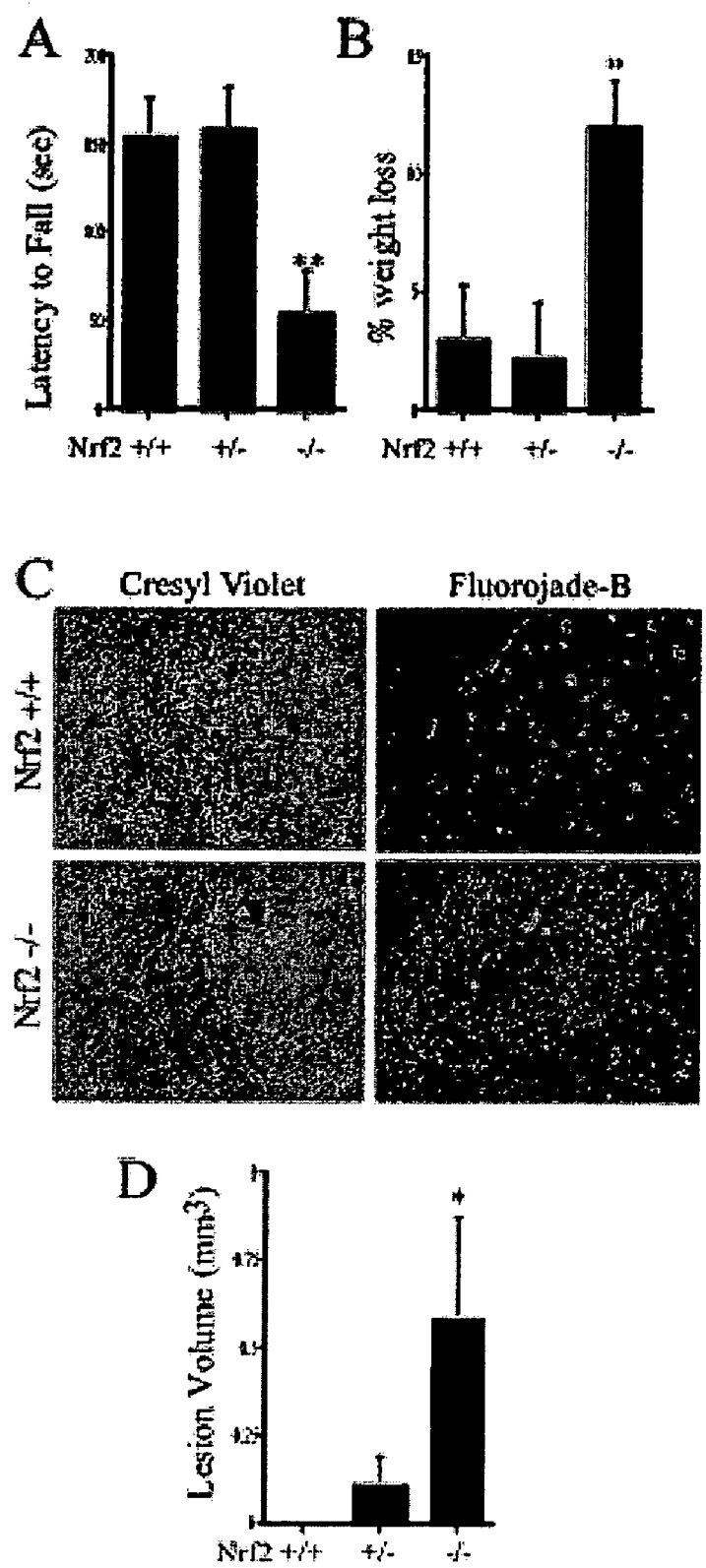
FIG. 3: Nrf2−/− mice are more vulnerable to 3NP in vivo. 3NP was administered (N=6 Nrf2+/+, 6 Nrf2+/−, 8 Nrf2−/−). Latency to fall on rotorod (A) and weight loss as a percent of starting weight (B) were measured four hours after the final injection. Cresyl violet (C left two panels) and fluorojade-B (C right two panels) were used to visualize lesions. Average lesion volume was calculated (D) on sections 200 µm apart. All data are average±SEM. *$p<0.05$ compared to WT, **$p<0.01$ compared to WT and heterozygous.

Four hours after the last dose, motor skills were assessed by rotarod performance. Up to three trials were given for each mouse and the longest time spent on the rotarod was used for analysis. All PBS-injected mice were able to maintain 5 rpm for 180 sec (the maximum time allowed). The only group that exhibited significant deficits as compared to the PBS-injected animals was the 3NP-injected Nrf2−/− group. Furthermore, the knockout mice had significantly reduced function when compared to 3NP-injected Nrf2+/+ and heterozygous mice (FIG. 3A). Likewise, the only group that differed significantly from their starting weight was the 3NP injected Nrf2−/− mice (FIG. 3B) who lost 12±1.9% of their starting weight.

After mice were sacrificed, brains were stained with cresyl violet or Fluorojade-B (FIG. 3C). Lesions in Nrf2−/− mice were observable using both staining methods; however, they were more apparent in the fluorojade B-stained sections; these sections were used for lesion volume quantification (FIG. 3D). No lesions were found in any of the Nrf2+/+ mice and only one Nrf2+/− mouse had a measurable lesion. Five of the eight treated Nrf2−/− mice were found to have measurable lesions.

In Vivo Sensitivity of Nrf2−/−, Nrf2+/− and Nrf2+/+ Mice to Malonate

Figure 4:
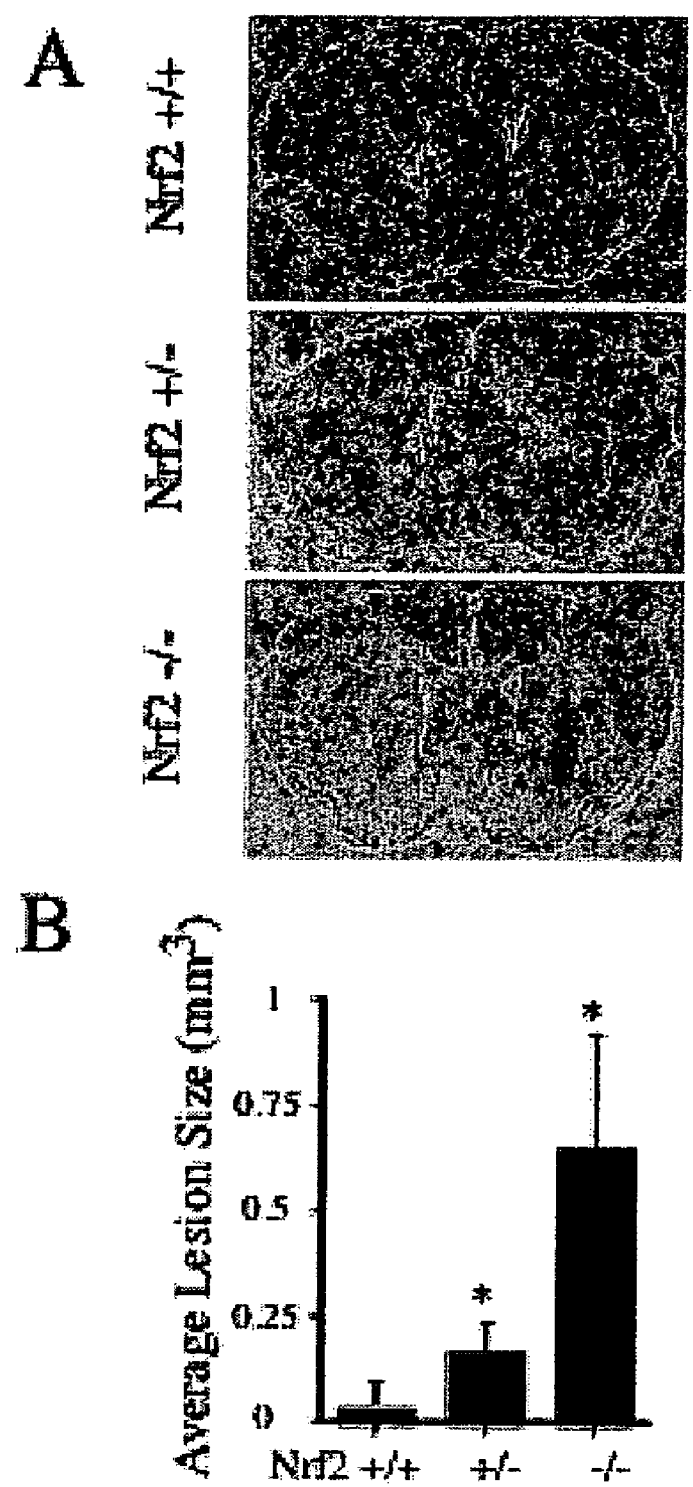
FIG. 4: Nrf2−/− mice are more vulnerable to malonate in vivo. Malonate was administered to the right striatum with a contralateral saline control (N=6 Nrf2+/+, 8 Nrf2+/−, 7 Nrf2−/−). Shown are representative sections of mice with lesions (A). Average lesion size was quantified (B). Data are average±SEM. *$p<0.05$ compared to WT.

Because of concerns about possible differences in systemic toxicity, metabolism, clearance, and blood brain barrier permeability between Nrf2−/− and Nrf2+/+ mice, we also examined sensitivity to intrastriatal malonate injection. Ten days post-injection mice were sacrificed and lesion size was measured by cresyl violet staining (FIG. 4A). None of the mice exhibited an overt behavioral phenotype; however both Nrf2−/− and Nrf2+/− mice had significantly larger lesions than Nrf2+/+. Average lesion size was increased over 21-fold in Nrf2−/− versus Nrf2+/+ mice and 4-fold in Nrf2−/− versus Nrf2+/− (Nrf2+/+0.03±0.07 $mm^3$; Nrf2+/−0.16±0.07 $mm^3$; Nrf2−/−0.65±0.27 $mm^3$). Only one Nrf2+/+ mouse had a measurable lesion. No lesions were found in the contralateral vehicle-injected hemisphere of any mouse (FIG. 4B).

Activation of ARE-hPAP Reporter as a Result of Toxin Administration

Figure 5:
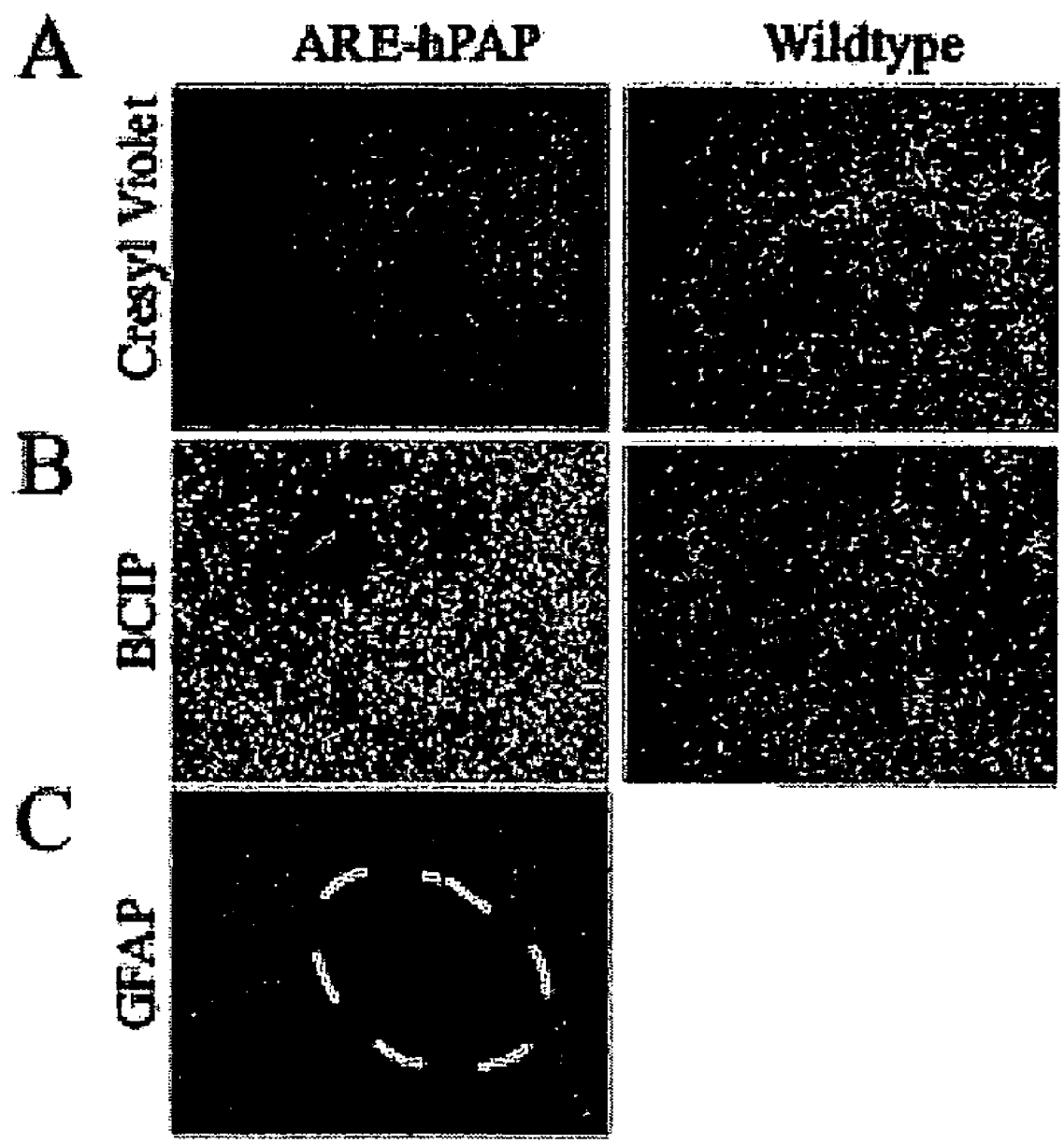
FIG. 5: hPAP reporter is expressed in penumbra of malonate induced lesion. Serial sections from malonate-lesioned ARE-hPAP reporter mice were stained with cresyl violet (A), hPAP histochemistry and nuclear fast red (B), and fluorescein-labeled GFAP (C).

Malonate was injected intrastriatally into ARE-hPAP reporter mice. After 48 hours the mice were euthanized and hPAP histochemistry was performed. FIG. 5 demonstrates that hPAP activity is present near the edges of the lesion (circumscribed by the dashed circles) as determined by cresyl violet and BCIP/tNBT staining of serial sections (FIGS. 5A, B). ARE-activated astrocytes, as visualized by GFAP immunohistochemistry, occur in a similar pattern (FIG. 5C).

Nrf2 Overexpression in Transplanted Astrocytes Protects from Malonate Lesions

Figure 6:
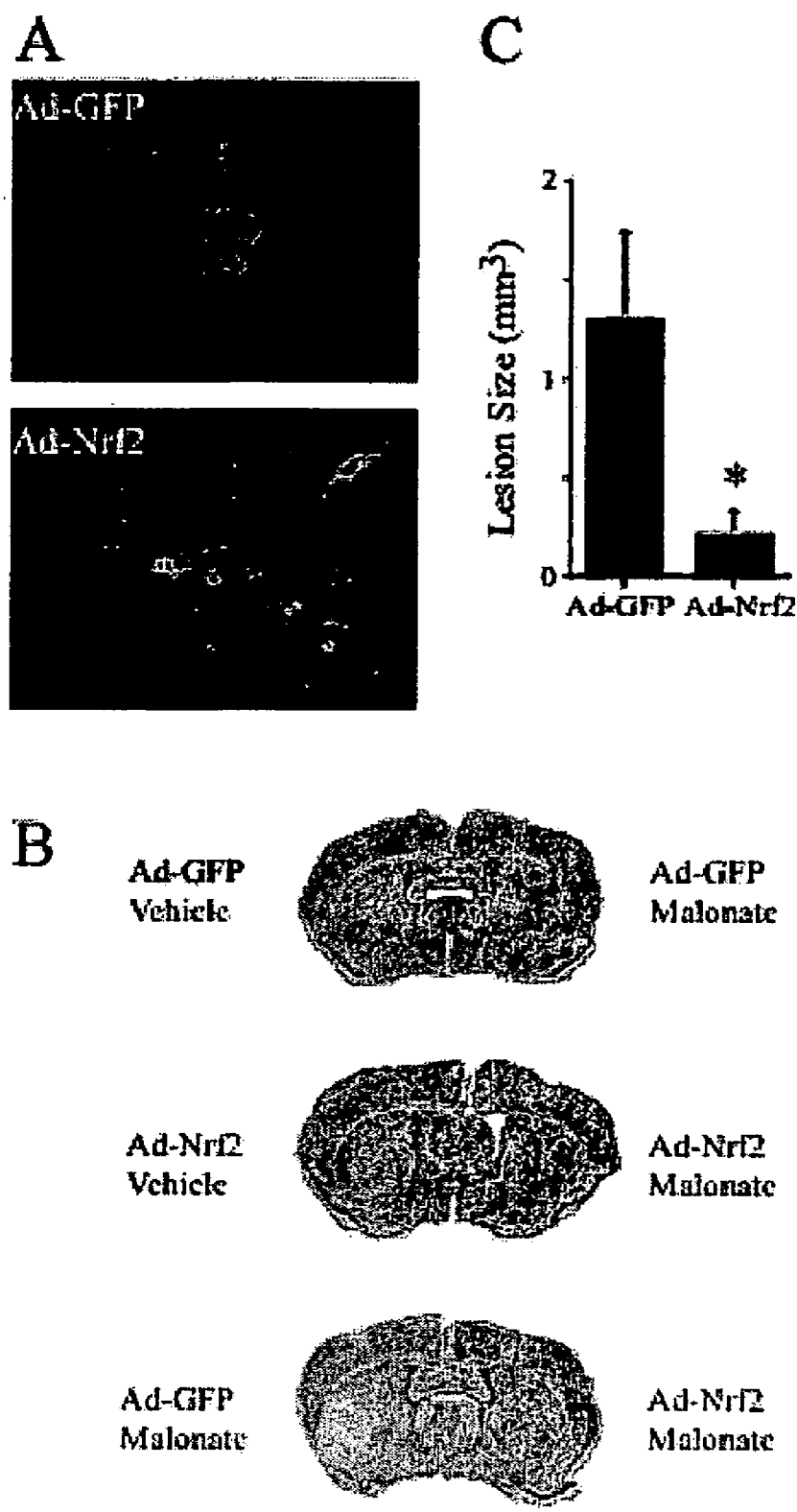
FIG. 6: Ad-Nrf2 infected astrocyte transplants protect from malonate induced lesions. hPAP+ astrocytes were infected with Ad-GFP or Ad-Nrf2-GFP. GFP expression and hPAP histochemistry were visualized (A). Mice were lesioned 5 weeks post-transplant with malonate. Lesions were visualized by cresyl violet (B) and quantified (C). *$p<0.05$ compared to hemispheres receiving GFP-infected astrocytes.

We tested the hypothesis that pre-activation of Nrf2 in vivo could protect from lesions caused by complex II inhibitors. In order to maintain Nrf2 overexpression long-term, primary astrocytes infected with adenoviral-Nrf2/GFP or the GFP control vector were injected into the striatum. Infection rates of the astrocytes approached 100% at 200MOI, as visualized by GFP expression. Only those astrocytes infected with the Nrf2 adenovirus demonstrated hPAP activity (FIG. 6A). Post-injection survival and migration of astrocytes was monitored by GFP expression. Migration of infected astrocytes away from the needle tract was limited, which is in agreement with published accounts of cortical astrocyte injections (Petit, A., et al., *J. Neurosci.* 21:7182-7193, 2001). After five weeks, mice were dosed with malonate as described above. Strikingly, hemispheres receiving Nrf2-infected astrocyte transplants were virtually resistant to malonate, whereas hemispheres receiving control astrocytes were no different than untransplanted controls (FIGS. 6B, C).

Discussion

In the current study, we have demonstrated the importance of Nrf2-mediated ARE induction due to complex II inhibition, a model of HD. The ARE is a cis-acting sequence in the promoter of many cytoprotective genes. In response to a variety of insults, the transcription factor Nrf2 interacts with the ARE to induce the expression of a multitude of genes including thioredoxin reductase-1, ferritin, heme-oxygenase-1 and peroxiredoxin (Lee, J. M., et al., supra, 2003; Shih, A. Y., et al., supra, 2003). These enzymes consequently increase levels of glutathione and NADPH, free radical scavenging, and other protective pathways. Nrf2−/− mice, lacking the ability to induce ARE-driven gene expression, are more susceptible to a variety of toxic insults in vivo (Chan, K. and Y. W. Kan, supra, 1999; Enomoto, A., et al., supra, 2001; Ramos-Gomez, M., et al., *Carcinogenesis* 24:461-467, 2003; Chan, K., et al., *Proc. Natl. Acad. Sci. USA* 98:4611-4616, 2001). Furthermore, Nrf2−/− mice are known to spontaneously develop hemolytic anemia and a lupus-like syndrome relatively late in life (L1, J., et al., supra, 2004; Lee, J. M., et al., *Proc. Natl. Acad. Sci. USA* 101:9751-9756, 2004; Yoh, K., et al., *Kidney Int.* 60:1343-1353, 2001). The wide array of tissues affected by Nrf2 deficiency suggests a strong role in general cellular protection. This is the first published account demonstrating that Nrf2−/− mice are more susceptible to neurotoxins in vivo.

Previously, we have shown that Nrf2 is a critical determinant of vulnerability to mitochondrial complex I inhibitors and calcium toxicity in vitro (Lee, J. M., et al., supra, 2003). Like complex I inhibition, complex II toxicity is known to involve oxidative stress and excitotoxicity (Bizat, N., et al., *J. Neurosci.* 23:5020-5030, 2003; Kim, G. W. and P. H. Chan, *J. Cereb. Blood Flow Metab.* 22:798-809, 2002). Consequently, we hypothesized that ARE-mediated transcription would also be important in protecting against complex II inhibition. Indeed, we found that Nrf2−/− neurons are more vulnerable to 3NP in vitro. This is likely due to Nrf2-dependent gene expression changes (Lee, J. M., et al., supra, 2003; Lee, J. M., et al., supra, 2003; Shih, A. Y., et al., supra, 2003; Kraft, A. D., et al., supra, 2004). In vivo, Nrf2−/−, +/−, and +/+ mice revealed vulnerability to 3NP exposure that inversely correlated with the number of intact Nrf2 alleles present.

3NP is typically administered systemically. To ensure that differential sensitivity in the knockout mice was due specifically to lack of Nrf2 and not to other factors that influence toxin delivery to the brain or systemic toxicity, we also assessed vulnerability to local malonate administration. Malonate produced a more uniform lesion while exhibiting the same inverse correlation between lesion size and number of Nrf2 alleles. We have found no indication that metabolism of either 3NP or malonate is influenced by Nrf2 deficiency. It is known that malonate is incorporated into the fatty acid biosynthesis pathway (Kim, Y. S., *J. Biochem. Mol. Biol.* 35:443-451, 2002). As fatty acid synthesis genes have not been identified as Nrf2-dependant targets in astrocytes or neurons (Lee, J. M., et al., supra, 2003; Lee, J. M., et al., supra, 2003; Kraft, A. D., et al., supra, 2004), it is unlikely that malonate metabolism is affected. Very little is known about the clearance of 3NP.

A differential sensitivity to complex II inhibitors between Nrf2−/− and Nrf2+/+ may exist due to baseline differences in Nrf2-driven gene expression or due to a lack of an inducible protective response. In primary neuronal cultures, we saw that ARE-dependant transcription occurs in surviving astrocytes at toxic doses of 3NP. Furthermore, we found that ARE-dependant transcription is also induced in vivo and is localized to the penumbra of the lesion formed by malonate injection; activated astrocytes are also seen in the penumbra. This suggests that in close association with neuronal death due to complex II inhibition, astrocyte populations mount a response that may involve activation of Nrf2 and ARE-dependant signaling. Current studies are exploring this phenomenon.

We proposed that additional ARE activation may provide further protection against complex II inhibition. Astrocytes engineered to express Nrf2 were injected into the striatum 5 weeks prior to lesioning. A proportion of transplanted cells survived and provided significant protection from malonate lesions. Only the transplanted cells had upregulated hPAP activity, indicating that a relatively small number of astrocytes overexpressing Nrf2 can protect against an acute insult. After 5 weeks, the ARE activity seen in the transplanted brains is principally due to the transplanted cells and not due to the transient trauma of injection which can activate the ARE transiently (data not shown).

There are currently no adequate approaches to the prevention and treatment of HD. The induction of ARE-dependant transcription is an exciting potential tool in the prevention of neurodegeneration. Further study as to the utility and mechanism of Nrf2-mediated protection by cell transplants is certainly warranted. The overwhelming protection seen in acute toxin exposure suggests that these transplants may be beneficial in genetic models of HD, where the insult is chronic and multifaceted. Such studies are currently in progress. In addition, chemical ARE activators may also be useful.

CONCLUSION

We have shown that Nrf2 deficiency renders mice more susceptible to complex II inhibition, a insult that can activate ARE-dependant transcription. Furthermore, pre-activation of the ARE in transplanted astrocytes can dramatically protect against complex II inhibition. Taken together, these data confirm Nrf2 and ARE-dependant signaling as a critical determinant of neurotoxicity both in vitro and in vivo.

Table 1: Phenotypic scoring of mice after 3NP administration. Nrf2+/+, Nrf2+/− and Nrf2−/− mice were scored Stage 0, I, II or III based on the development of clinical symptoms.

TABLE 1

|  | Stage | | | |
| --- | --- | --- | --- | --- |
|  | 0 | I | II | III |
| Nrf2+/+ | 5 | 1 | — | — |
| Nrf2+/− | 4 | 2 | — | — |
| Nrf2−/− | 1 | 3 | 1 | 3 |

Example II

Demonstration of Nrf-2-mediated Protection in Murine Neural Progenitor Cells

Murine neural progenitor cells (NPC) were utilized to deliver the therapeutic effects of Ad-Nrf2 mediated protection in vivo. NPC cultures were derived from approximately E11.5 mouse embryos. Animals were mated for 24 hours and after 12 days pregnant females were sacrificed and embryos were isolated. The frontal neural tube was dissected from each individual embryo and cells were cultured similarly to human NPC as described (L1, J., et al., 2005, *J Neurochem.* 92:462-76).

NPC were grafted twenty-four hours after infection with either Ad-GFP or Ad-Nrf2. Fifty MOI of virus was added to serum free NPC cultures and left until cells were prepared for transplantation. Just prior to transplantation, NPC were centrifuged, washed at least once with growth media centrifuged again and concentrated in growth medium to approximately 20,000 cells/µl. Cells were counted by dissociating an aliquot of the concentrated culture before and after transplantation. Concentrated cells were kept on ice until transplantation (usually within one to two hours). Infected whole neurospheres (1 µl; 20,000 cells) were grafted according to the same striatal coordinates as astrocyte grafts (0.5 mm anterior to bregma, 2.1 mm lateral to midline, 3.8 mm ventral to bone surface).

Two weeks after transplants were made, the mice were lesioned with malonate as described (1 µl; 0.75M into the coordinates reported). It is known that neural stem cells can provide protection against mitochondrial complex II inhibition (Madhavan, et al., 2005, *Ann N Y Acad. Sci.* 1049:185-8). In our experiments, this phenomenon was observed although not quantified. Animals grafted with Ad-GFP-infected NPC appeared to incur markedly less severe lesions than those that received no graft at all.

Figure 7:
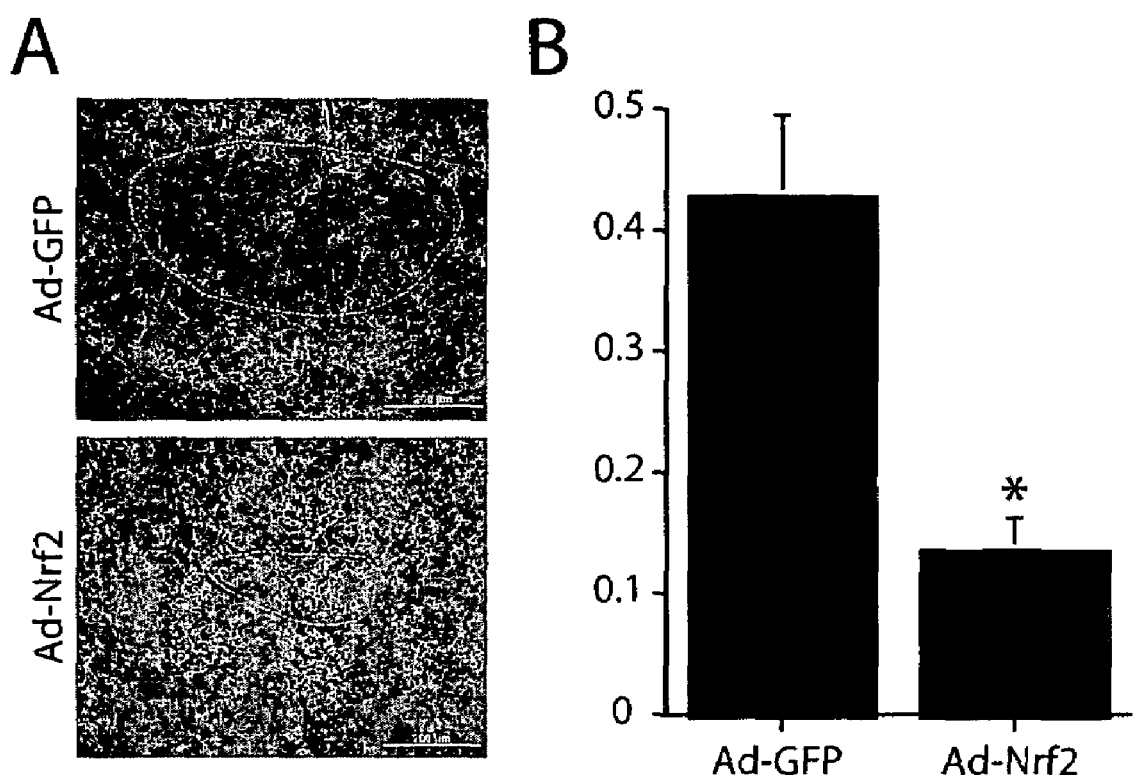
FIG. 7: Ad-Nrf2 infected neural progenitor cell (NPC) grafts are protective against malonate lesioning compared to Ad-GFP infected NPC grafts. (A) Cresyl violet stained representative examples of malonate lesions made two weeks after grafting with Ad-GFP or Ad-Nrf2 infected NPC. (B) Average lesion size±SEM, $p<0.05$ compared to Ad-GFP grafted animals.

We find that in addition to any protection mediated by NPC transplantation alone, there is additional protection conferred when NPC are infected with Ad-Nrf2 prior to transplantation (0.428±0.067 Ad-GFP, N=4, compared to 0.135±0.029 Ad-Nrf2, N=3, $p<0.05$; FIG. 7). Lesions were quantified using the Cavalieri estimator in the Stereo Investigator software (Microbrightfield, Williston, Vt.). This observation supports our general observation that Nrf2-overexpressing cells grafted into the brain are protective against neurotoxicity. Additionally this result provides evidence that the grafted cells may be derived from multiple sources.

We claim:

1. A method of diminishing the symptoms of Huntington's Disease in a patient, comprising the steps of:
   (a) identifying a patient with symptoms of Huntington's Disease,
   (b) producing a cell culture, wherein the cell culture comprises astrocyte or neural progenitor cells with NF-E2 related factor-2 (Nrf-2) induced antioxidant response element (ARE) mediated transcription, and
   (c) transplanting at least a portion of the cell culture into the striatum of the patient, wherein symptoms of Huntington's Disease are diminished.

2. The method of claim 1 wherein the astrocyte cells are human-derived primary astrocytes.

3. The method of claim 1 wherein the ARE mediated transcription is induced by infection of the cells with a vector comprising an ARE-inducing Nrf-2 transgene.

4. The method of claim 3 wherein the transgene is human Nrf-2.

5. The method of claim 4 wherein the transgene is SEQ ID NO:1.

6. The method of claim 3 wherein the vector is a lentivirus.

7. The method of claim 3 wherein the vector is selected from the group of adeno-viruses, adeno-associated viruses and lentiviruses.

8. The method of claim 1 where ARE induced transcription is induced through chemical methods.

9. The method of claim 8 wherein the chemical is selected from the group consisting of tert-butylhydroquinone, sulforaphane, curcumin, and diethylmaleate.

10. The method of claim 8 wherein the chemical is selected from the group consisting of (i) oxidizable diphenols and quinines; (ii) Michael reaction acceptors (olefins or acetylenes conjugated to electron-withdrawing groups); (iii)

isothiocyanates; (iv) hydroperoxides; (v) trivalent arsenic derivatives; (vi) divalent heavy metal cations (Hg2+, Cd2+); (vii) vicinal dithiols; (viii) 1,2-dithiole-3-thiones; and (ix) carotenoids and other conjugated polyenes.

11. The method of claim 1 additionally comprising the step of evaluating the symptoms of Huntington's Disease.

12. The method of claim 11 wherein the evaluation comprises assessment of transplant survival.

13. The method of claim 11 wherein the evaluation comprises evaluation of progression of disease after transplant.

14. The method of claim 1 wherein the cells to be transplanted are at $5 \times 10^6$ cells/240 ml media (±10%).

15. A method of increasing antioxidant response element (ARE)-mediated transcription in a patient, comprising the steps of:

(a) identifying a patient with symptoms of Hungtington's Disease, (b) producing a cell culture, wherein the cell culture comprises astrocyte or neural progenitor cells with NF-E2 related factor-2 (Nrf-2) induced ARE-mediated transcription, and (c) transplanting at least a portion of the cell culture into the striatum of the patient, wherein Nrf-2 induced ARE-mediated transcription is increased.

16. The method of claim 15 wherein the astrocyte cells are human-derived primary astrocytes.

17. The method of claim 15 wherein the ARE-mediated transcription is induced by infection of the cells with a vector comprising an ARE-inducing Nrf-2 transgene.

* * * * *

UNITED STATES PATENT AND TRADEMARK OFFICE
CERTIFICATE OF CORRECTION

PATENT NO. : 7,638,119 B2
APPLICATION NO. : 11/290293
DATED : November 30, 2005
INVENTOR(S) : Jeffrey A. Johnson It is certified that error appears in the above-identified patent and that said Letters Patent is hereby corrected as shown below:

Column 1, line 46, "Neuroloqy" should be --Neurology--

Column 3, line 6, "L1" should be --LI--

Column 15, line 29, "L1" should be --LI--

Signed and Sealed this

Fifteenth Day of June, 2010

David J. Kappos
*Director of the United States Patent and Trademark Office*

SEQUENCE LISTING

```
<160> NUMBER OF SEQ ID NOS: 1

<210> SEQ ID NO 1
<211> LENGTH: 2439
<212> TYPE: DNA
<213> ORGANISM: Homo sapiens

<400> SEQUENCE: 1
gcagccgcca  ccgccgccgc  cgccgccacc  agagccgccc  tgtccgcgcc  gcgcctcggc       60
agccggaaca  gggccgccgt  cggggagccc  caacacacgg  tccacagctc  atcatgatgg      120
acttggagct  gccgccgccg  ggactcccgt  cccagcagga  catggatttg  attgacatac      180
tttggaggca  agatatagat  cttggagtaa  gtcgagaagt  atttgacttc  agtcagcgac      240
ggaaagagta  tgagctggaa  aaacagaaaa  aacttgaaaa  ggaaagacaa  gaacaactcc      300
aaaaggagca  agagaaagcc  tttttcgctc  agttacaact  agatgaagag  acaggtgaat      360
ttctcccaat  tcagccagcc  cagcacatcc  agtcagaaac  cagtggatct  gccaactact      420
cccaggttgc  ccacattccc  aaatcagatg  ctttgtactt  tgatgactgc  atgcagcttt      480
tggcgcagac  attcccgttt  gtagatgaca  atgaggtttc  ttcggctacg  tttcagtcac      540
ttgttcctga  tattcccggt  cacatcgaga  gcccagtctt  cattgctact  aatcaggctc      600
agtcacctga  aacttctgtt  gctcaggtag  ccctgttga   tttagacggt  atgcaacagg      660
acattgagca  agtttgggag  gagctattat  ccattcctga  gttacagtgt  cttaatattg      720
aaaatgacaa  gctggttgag  actaccatgg  ttccaagtcc  agaagccaaa  ctgacagaag      780
```

-continued

```
ttgacaatta tcatttttac tcatctatac cctcaatgga aaaagaagta ggtaactgta      840
gtccacattt tcttaatgct tttgaggatt ccttcagcag catcctctcc acagaagacc      900
ccaaccagtt gacagtgaac tcattaaatt cagatgccac agtcaacaca gattttggtg      960
atgaatttta ttctgctttc atagctgagc ccagtatcag caacagcatg ccctcacctg     1020
ctactttaag ccattcactc tctgaacttc taaatgggcc cattgatgtt tctgatctat     1080
cactttgcaa agctttcaac caaaaccacc ctgaaagcac agcagaattc aatgattctg     1140
actccggcat ttcactaaac acaagtccca gtgtggcatc accagaacac tcagtggaat     1200
cttccagcta tggagacaca ctacttggcc tcagtgattc tgaagtggaa gagctagata     1260
gtgcccctgg aagtgtcaaa cagaatggtc ctaaaacacc agtacattct tctggggata     1320
tggtacaacc cttgtcacca tctcaggggc agagcactca cgtgcatgat gcccaatgtg     1380
agaacacacc agagaaagaa ttgcctgtaa gtcctggtca tcggaaaacc ccattcacaa     1440
aagacaaaca ttcaagccgc ttggaggctc atctcacaag agatgaactt agggcaaaag     1500
ctctccatat cccattccct gtagaaaaaa tcattaacct ccctgttgtt gacttcaacg     1560
aaatgatgtc caaagagcag ttcaatgaag ctcaacttgc attaattcgg gatatacgta     1620
ggaggggtaa gaataaagtg gctgctcaga attgcagaaa aagaaaactg gaaaatatag     1680
tagaactaga gcaagattta gatcatttga aagatgaaaa agaaaaattg ctcaaagaaa     1740
aaggagaaaa tgacaaaagc cttcacctac tgaaaaaaca actcagcacc ttatatctcg     1800
aagttttcag catgctacgt gatgaagatg gaaaacctta ttctcctagt gaatactccc     1860
tgcagcaaac aagagatggc aatgttttcc ttgttcccaa aagtaagaag ccagatgtta     1920
agaaaaacta gatttaggag gatttgacct tttctgagct agttttttttg tactattata     1980
ctaaaagctc ctactgtgat gtgaaatgct catactttat aagtaattct atgcaaaatc     2040
atagccaaaa ctagtataga aaatataacg aaactttaaa aagcattgga gtgtcagtat     2100
gttgaatcag tagtttcact ttaactgtaa acaatttctt aggacaccat ttgggctagt     2160
ttctgtgtaa gtgtaaatac tacaaaaact tatttatact gttcttatgt catttgttat     2220
attcatagat ttatatgatg atatgacatc tggctaaaaa gaaattattg caaaactaac     2280
cactatgtac ttttttataa atactgtatg gacaaaaaat ggcattttttt atattaaatt     2340
gtttagctct ggcaaaaaaa aaaaatttta agagctggta ctaataaagg attattatga     2400
ctgttaaaaa aaaaaaaaaa aaaaaaaaaa aaaaaaaa                             2439
```